United States Patent [19]
Tochigi et al.

[11] Patent Number: 4,586,819
[45] Date of Patent: May 6, 1986

[54] LASER RAMAN MICROPROBE

[75] Inventors: Kenji Tochigi; Yoshiaki Hanyu; Yutaka Hiratsuka, all of Yokohama, Japan

[73] Assignee: Hitachi, Ltd., Tokyo, Japan

[21] Appl. No.: 510,912

[22] Filed: Jul. 5, 1983

[30] Foreign Application Priority Data

Jul. 9, 1982 [JP] Japan ................................ 57-118514
Oct. 6, 1982 [JP] Japan ................................ 57-174529
Dec. 10, 1982 [JP] Japan ................................ 57-215404

[51] Int. Cl.⁴ .......................... G01J 3/44; G01N 21/65
[52] U.S. Cl. ..................................... 356/301; 356/318
[58] Field of Search ............... 356/301, 317, 318, 417, 356/73; 350/166, 502, 508, 509, 511, 523, 524; 250/459.1, 461.1, 461.2, 458.1

[56] References Cited

U.S. PATENT DOCUMENTS

| | | | |
|---|---|---|---|
| 3,205,767 | 9/1965 | Weber et al. | 350/502 |
| 3,421,806 | 1/1969 | Weber | 350/502 |
| 3,566,114 | 2/1971 | Brewer | 250/461.2 |
| 3,820,870 | 6/1974 | Smith | 350/511 |
| 3,887,283 | 6/1975 | Merstallinger et al. | 350/511 |
| 4,125,828 | 11/1978 | Resnick et al. | 250/461.2 |
| 4,182,574 | 1/1980 | Quillfeldt | 356/318 |
| 4,195,930 | 4/1980 | Delhaye et al. | 356/301 |
| 4,407,008 | 9/1983 | Schmidt et al. | 356/301 |
| 4,444,317 | 4/1984 | Wick et al. | 356/318 |
| 4,476,870 | 10/1984 | Peterson et al. | 250/458.1 |

FOREIGN PATENT DOCUMENTS

0918088  2/1963  United Kingdom ................ 350/33
2039031  7/1980  United Kingdom ................ 356/417

OTHER PUBLICATIONS

Mole Brochure, Instruments SA, Inc. 11/76.
*Zeitschrift fur Wissenschaftliche Mikroskopie*, Ploem, J. S., vol. 68, 1967, pp. 129-142.
"A Laser Microscope," Peppers, N. A., *Applied Optics*, vol. 4, No. 5, p. 555, 5/65.
"Raman Measurements of Stress in Silicon-on-Sapphire Device Structures," Brueck, S. R. and others, *Appl. Phys. Lett.*, vol. 40, 5/15/82, p. 895.
"A High Frequency Kerr-Effect Microscope for Bubble Devices," Harrison, Colin G., and others, *IEEE Transactions on Instrumentation and Measurement*, vol. IM-30, No. 3, 9/81, p. 202.
"New Developments in Raman Spectrometry," Delhaye, M., and others *Proc. Soc. Photo-Opt. Instrum. Eng.*, vol. 236, p. 24.

*Primary Examiner*—F. L. Evans
*Assistant Examiner*—Joel L. Harringa
*Attorney, Agent, or Firm*—Antonelli, Terry & Wands

[57] ABSTRACT

A laser Raman microprobe separates a laser beam reflected by a sample and a Raman scattered light generated by the sample by a filter which transmits or reflects a light in a predetermined wavelength region including a wavelength region of the reflected laser beam and applies only the Raman scattered light separated by the filter to a single-monochromator for spectroanalysis. A high sensitivity analysis is attained by the single-monochromator.

14 Claims, 6 Drawing Figures

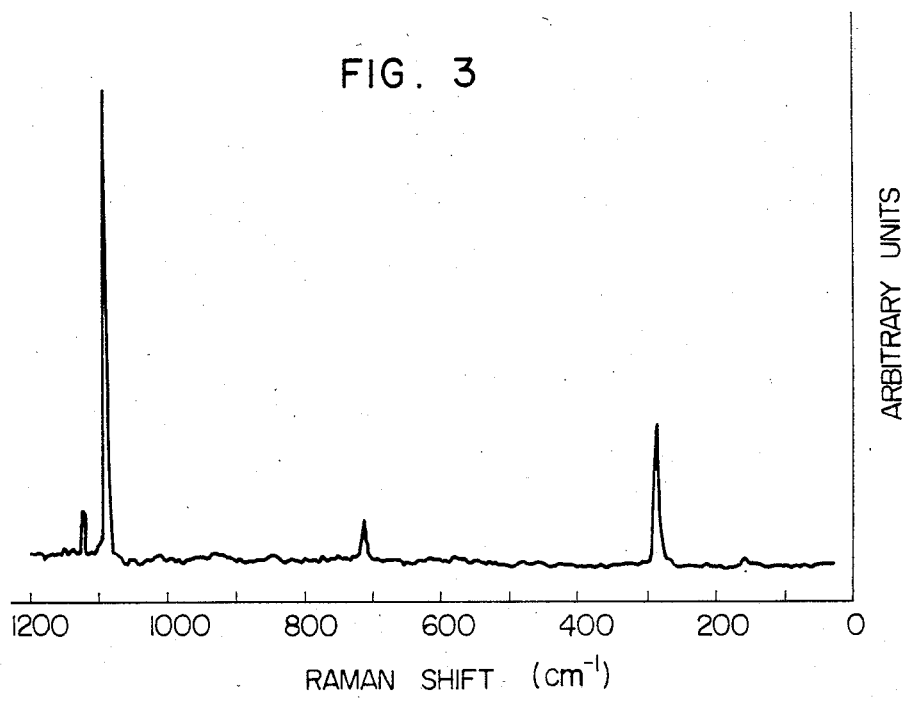
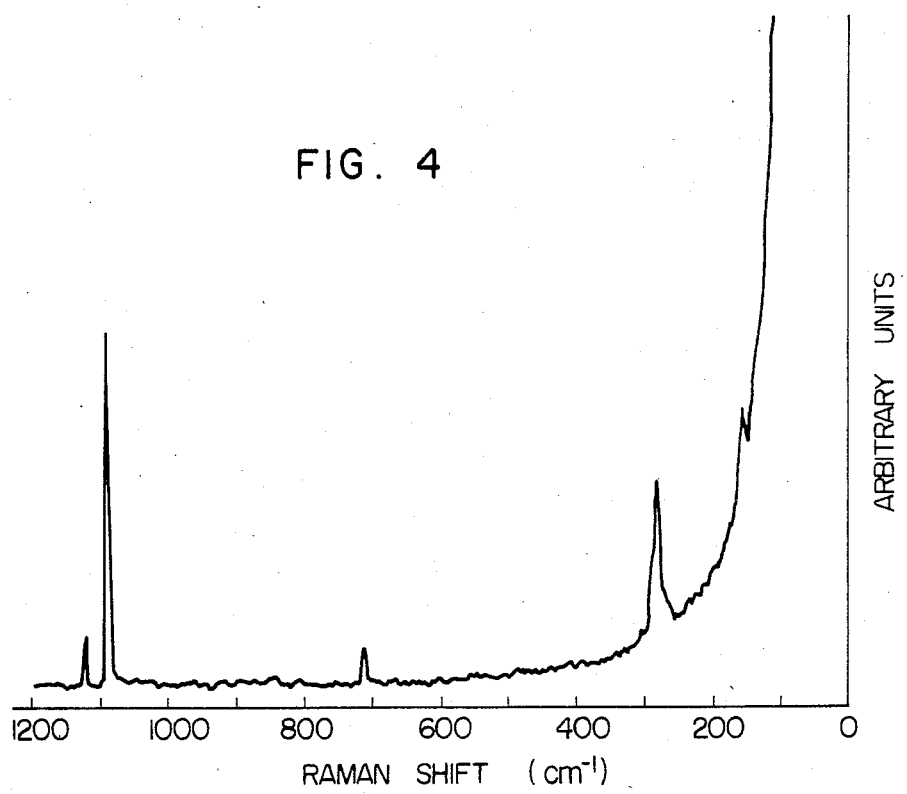

LASER RAMAN MICROPROBE

BACKGROUND OF THE INVENTION

The present invention relates to a Raman spectroanalyzer, and more particularly to a laser Raman microprobe which enables analysis of a fine sample.

The laser Raman microprobe is disclosed, for example, in U.S. Pat. No. 4,195,930 to Delhaye et al. In this device, a laser beam generated by a laser oscillator is irradiated to a sample through a microscope and a light applied to the microscope, of a Raman scattered light emanated from the sample and a reflected laser beam from the sample is split by a splitting prism. One of the two split components is directed to a screen to display an enlarged image of the sample on the screen. The other component is directed to a double monochromator where it is analyzed, and the light is applied to a photomultiplier to convert it to an electrical signal. By recording and reading the electrical signal, the sample is quantatively and qualitatively analyzed.

In this device, in order to perpendicularly irradiate the sample by the laser beam, a ring-shaped mirror or a disc-shaped half-mirror is arranged in the microscope. When the ring-shaped mirror is used a fine sample such as several tens microns or several microns in diameter cannot be analyzed because a condensed laser beam by the microscope is several hundreds microns in diameter. On the other hand, when the disc-shaped half-mirror is used, the condensed laser beam diameter by the microscope is in the order of 1 micron and a sample larger than 1 micron in diameter can be analyzed. However, when the half-mirror is used, the Raman scattered light from the sample is reduced to one half by the half-mirror and further reduced to one half by the splitting prism and hence the analysis sensitivity is lowered. In addition, since the Raman scattered light as well as the reflected laser beam is applied to the double-monochromator, the reflected laser beam must be removed by the double-monochromator and the device is of large scale and expensive.

SUMMARY OF THE INVENTION

It is an object of the present invention to provide a laser Raman microprobe which can analyze a fine sample with high sensitivity.

It is another object of the present invention to provide a compact and inexpensive laser Raman microprobe.

In order to achieve the above objects, in accordance with an aspect of the present invention, there is provided a filter for transmitting or reflecting a light in a predetermined wavelength range including the reflected laser beam in an optical path of the Raman scattered light and the reflected laser beam transmitted through the microscope so that the predetermined range of light including the reflected laser beam and the Raman scattered light are separated by the filter and the Raman scattered light free from the reflected laser beam is applied to a single-monochromator to enable analysis of a fine sample such as foreign matters of 1 $\mu$ or less in diameter on an IC wafer with high sensitivity.

BRIEF DESCRIPTION OF THE DRAWINGS

FIG. 3 is a spectrum chart of one example of analysis of a sample by the laser Raman microprobe of the present invention, FIG. 4 is a spectrum chart of a comparative example analyzed by a double-monochromator which is not in accordance with the present invention.

DESCRIPTION OF THE PREFERRED EMBODIMENT

One embodiment of the present invention will now be explained with reference to the drawings.

Figure 1:
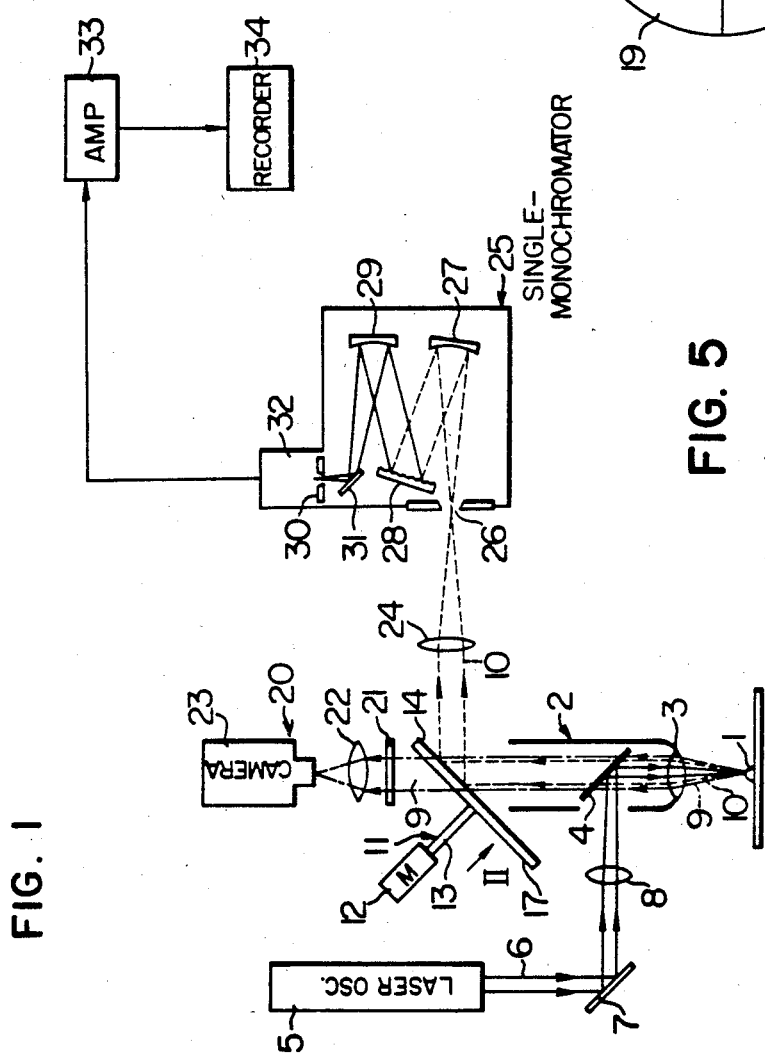
FIG. 1 is a conceptual view of a laser Raman microprobe for illustrating a principle of the present invention.

FIG. 1 shows an embodiment of the laser Raman microprobe of the present invention. In FIG. 1, an object lens 3 is arranged at a lower end of a microscope 2 which faces a sample 1, and a half-mirror 4 is arranged above the object lens 3 and a window is formed at the sidewall of the microscope 2 so as to enable a laser beam to pass through the sidewall and impinge upon the half-mirror 4. A laser oscillator 5 can change a wavelength of a generated laser beam 6. A mirror 7 is arranged in an optical path of the laser beam 6 generated by the laser oscillator 5, and reflects the laser beam 6 toward the half-mirror 4. A condenser lens 8 is arranged between the mirror 7 and the half-mirror 4 in the optical path of the laser beam 6 and condenses the laser beam 6 on the sample 1 in cooperation with the object lens 3. The mirror 7, the lens 8, the window and the half-mirror 4 are aligned with one another. Accordingly, the laser beam 6 generated by the laser oscillator 5 is reflected by the mirror 7, transmits through the condenser lens 8, passes through the window, enters into the microscope 2, reflected by the half-mirror 4, transmits through the object lens 3 and is focused onto the sample 1. A portion of the laser beam 6 focused on the sample 1 is reflected by the sample 1 to produce a reflected laser beam 9 and the other portion of the laser beam 6 excites the sample 1 to generate a Raman scattered light 10. Light separation means 11 is arranged in the optical path of the reflected laser beam 9 and the Raman scattered light 10 transmitted through the object lens 3 and the half-mirror 4. The light separation means 11 comprises a pulse motor 12 and six filters 14, 15, 16, 17, 18 and 19 supported on a rotary shaft 13 of the pulse motor 12. The filters 14–19 may be dichroic mirrors or band-pass filters having different transmission light wavelength bands, and one of them is disposed to extend across the optical path of the reflected laser beam 9 and the Raman scattered light 10. The filters 14–19 may be commercially available filters of e.g. a dielectric-coated glass structure, and are selected to transmit the predetermined wavelength band including the reflected laser beam 9. In order to observe the sample 1, observing means 20 is arranged in the optical path of the reflected laser beam 9 separated by the light separation means 11. The observing means 20 comprises a light attenuating filter 21 for attenuating the reflected laser beam 9, a condenser lens 22 for condensing the light transmitted through the attenuating filter 21, a camera 23 and a television receiver (not shown) so that an image of the sample 1 under analysis is displayed on the television receiver. The condenser lens 24 is arranged in the optical path of the Raman scattered light 10 separated by the light separation means 11 to condense the Raman scattered light 10. A single monochromator 25 has its inlet slit 26 arranged at a focal point of the condenser lens 24. Arranged in the single monochromator 25 are a first collimator 27 for reflecting the Raman scattered light 10 inputted from the inlet slit 26, a diffraction grating 28 which receives the Raman scattered light 10 reflected by the collimator 27 and produces spectra thereof, a second collimator 29 for reflecting the spectra from the diffraction grid 28 and a reflection mirror 31 which reflects the spectra from the collimator 29 toward an outlet slit 30. The diffraction grating 28 is rotatably supported in the single monochromator 25 and rotated by a drive mechanism not shown. A photomultiplier 32 is mounted to face the outlet slit 30 of the monochromator 25 and receives the spectra from the monochromator 25 and converts them to an electrical signal. An amplifier 33 is connected to the photomultiplier 32 and amplifies the electrical signal supplied from the photomultiplier 32 to a desired level. A recorder 34 is connected to the amplifier 33 and records the electrical signal supplied from the amplifier 33.

In the above arrangement, the sample 1 is positioned at the focusing point of the object lens 3 of the microscope and the wavelength of the laser beam generated by the laser oscillator 5 and the filter 14 to be used are set.

The laser oscillator 5 is activated to generate the laser beam 6. Thus, the laser beam 6 is reflected by the mirror 7, transmits through the lens 8, enters into the microscope 2 via the window, reflected by the halfmirror 4, transmits through the lens 3 and focused onto the sample 1. A portion of the laser beam 6 impinged to the sample 1 is reflected by the sample 1 to produce the reflected laser beam 9. The other portion of the laser beam 6 impinged to the sample 1 excites the sample 1 to generate the Raman scattered light 10. Portions of the reflected laser beam 9 and the Raman scattered light 10 are applied to the object lens 3, transmit through the half-mirror 4 and impinge to the filter 14. The light in the predetermined wavelength band including the reflected laser beam 9 transmits through the filter 14 and the other Raman scattered light 10 is reflected by the filter 14.

The reflected laser beam 9 transmitted through the filter 14 transmits through the attenuating filter 21 and the condenser lens 22 and enters into the camera 23 so that an enlarged image of the sample 1 is displayed on the television receiver.

On the other hand, the Raman scattered light reflected by the filter 14 transmits through the condenser lens 24, is focused to the inlet slit 26 of the monochromator 25 and enters into the monochromator 25. The Raman scattered light 10 spectroanalyzed by the single monochromator 25 passes through the outlet slit 30 and is applied to the photomultiplier 32 where it is converted to an electrical signal. The electrical signal is amplified by the amplifier 33 and then supplied to the recorder 34, which records the electrical signal.

Figure 6:
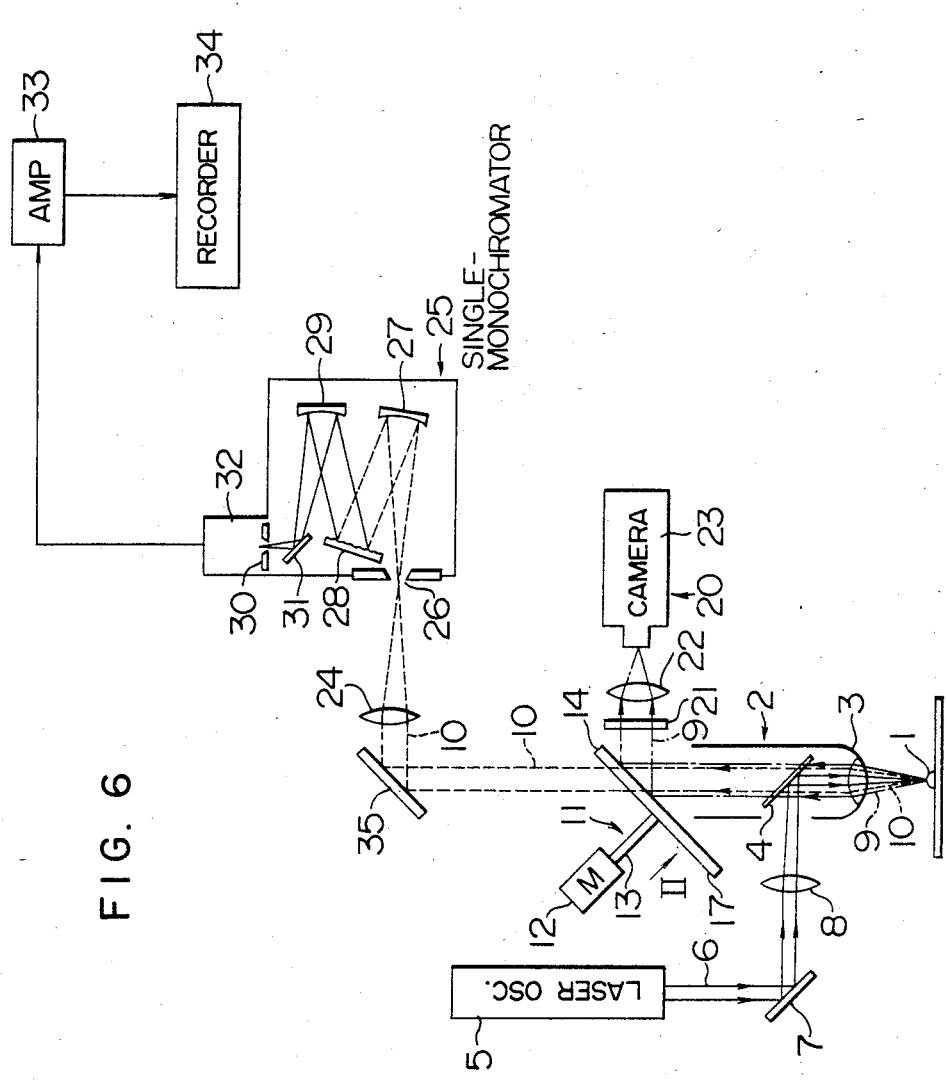
FIG. 6 illustrates another embodiment of the present invention.

The positions of the single-monochromator 25 and the observing means 20, as illustrated in FIG. 1, may be interchanged with the filter 14 being arranged to separate the reflected laser beam 9 and the Raman scattered light 10 so that the Raman scattered light 10 is transmitted through the filter 14 and via a mirror 35 through the condenser lens 24 to the single-monochromator 25 while the reflected laser beam 9 is reflected by the filter 14 to the camera 23 via the attenuating filter 21 and condenser lens 22 as shown in FIG. 6.

FIG. 3 shows a spectrum chart obtained for a sample of calcium carbonate ($CaCO_3$) having a diameter of 3 $\mu$m by irradiating a laser beam having a wavelength of 514.5 nm to the sample. FIG. 4 shows a spectrum chart for a sample of the same condition but without filter and with a double-monochromator substantially as in the above-referenced U.S. patent.

As seen from the composition of FIGS. 3 and 4, an effect of the reflected laser beam is not observed in FIG. 3 and the analysis of the light having the Raman shift of 10 $cm^{-1}$ is possible. In FIG. 4, an influence by stray light due to the reflected laser beam appears in the range of the Raman shift of 100–600 $cm^{-1}$ and the analysis is impossible in the range of the Raman shift of 0–200 $cm^{-1}$.

In the present embodiment by the use of the filter 14 (15–19), the stray light due to the reflected laser beam which cannot be eliminated by the double-monochromator is completely eliminated accordingly, an inexpensive and compact laser Raman microprobe can be provided.

While the six filters 14–19 are radially arranged in the light separation means 11 in the above embodiment, only one filter may be arranged or a plurality of filters may be movably arranged in a line or lines and they may be selectively used.

Figure 2:
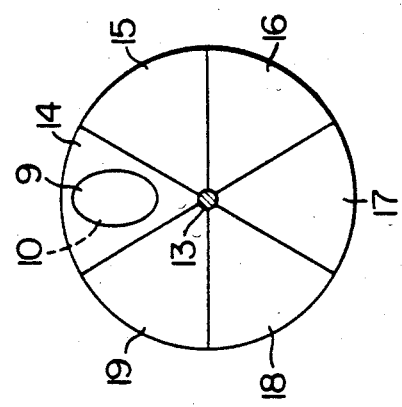
FIG. 2 is a view of a filter of FIG. 1 as viewed in a direction of an arrow II.
Figure 5:
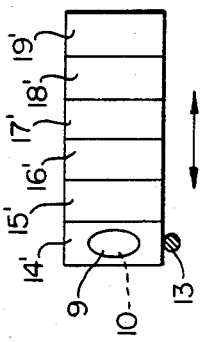
FIG. 5 illustrates a plurality of filters arranged in at least one line.

The filters 14–19 may reflect the light in the predetermined wavelength band including the laser beam. FIG. 5 illustrates a plurality of filters 14'–19' arranged in at least one line. In such arrangement, the filters may be driven in a linear manner in place of the rotational movement illustrated in FIGS. 1 and 2.

In general, when the laser beam is irradiated to the sample to generate the Raman scattered light from the sample, an intensity of the Raman scattered light is inversely proportional to fourth power of the wavelength of the laser beam (for a given intensity of the laser beam). Accordingly, in order to intensify the Raman scattered light, it is desirable to irradiate the sample with a laser beam of a short wavelength. However, the sample irradiated by the laser beam absorbs a portion of the laser beam and is heated by an energy thereof. The absorption of the laser beam by the sample tends to be larger as the wavelength of the laser beam is shorter accordingly, if the sample to be analyzed is of a material such as an organic material which is modified by heat, it is difficult to analyze the sample by using the laser beam having the short wavelength. Thus, it is necessary to select the laser beam (wavelength) depending on the material of the sample to be analyzed. By arranging the laser oscillator 5 which can generate variable wavelength of the laser beam 2 and the light separation means 11 having the plurality of filters 14–19 and linking the laser oscillator 5 to the light separation means 11, as shown in the embodiment, the laser beam can be switched depending on the material of the sample 1 and the analysis is facilitated.

By using narrow band band-pass filters as the filters 14–19 for separating the wavelength bands of the laser beam, spectra in shorter and longer wavelength regions than the wavelength of the laser beam can be obtained. By comparing the spectra in these wavelength regions, a temperature of the sample under analysis can be exactly detected. Accordingly, it is possible to determine whether an amorphous sample has been crystallized during the analysis and an exact analysis is attained. A relation between a phase of the sample and the result of analysis is clearly defined and reliability of the analysis is greatly enhanced.

We claim:

1. A laser Raman microprobe for analyzing a sample comprising:
   a microscope;
   a laser oscillator;
   laser directing means for directing a laser beam generated by said oscillator to the sample through said microscope;
   an optical system for passing along at least a portion thereof in combination both a laser beam reflected by the sample and applied to the microscope and Raman scattered light generated by the sample and applied to the microscope,
   said optical system including filter means disposed at an angle in an optical path the reflected laser beam and the Raman scattered light for separating the reflected laser beam and the Raman scattered light having wavelengths dependent upon the wavelength of said laser oscillator; and
   a sample analyzer including a single-monochromator coupled to said optical system for analyzing the sample based on a resulting spectrum;
   said filter means directing the separated Raman scattered light directly to said single-monochromator.

2. A laser Raman microprobe according to claim 1, wherein said filter means is a dichroic mirror for transmitting the light in a short wavelength region including the wavelength region of the reflected laser beam and for reflecting the Raman scattered light.

3. A laser Raman microprobe according to claim 1, wherein said filter means is a band-pass filter for transmitting the light in the wavelength region of the reflected laser beam and for reflecting the Raman scattered light.

4. A laser Raman microprobe for analyzing a sample comprising:
   a microscope;
   a laser oscillator;
   laser directing means for directing a laser beam generated by said laser oscillator to the sample through the microscope;
   an optical system for passing along at least a portion thereof both a laser beam reflected by the sample and applied to the microscope and Raman scattered light generated by the sample and applied to the microscope in combination,
   said optical system including separation means for separating the reflected laser beam from the Raman scattered light passed in combination, said separation means including a plurality of filters for transmitting or reflecting different wavelength regions of light, one of said filters being disposed in an optical path of the combination of the reflected laser beam and the Raman scattered light for separating the Raman scattered light; and
   a sample analyzer including a single-monochromator coupled to said optical system and analyzing the sample based on a resulting spectrum;
   said one of said filters being disposed for applying substantially only the Raman scattered light to said single-monochromator.

5. A laser Raman microprobe according to claim 4, wherein said plurality of filters are dichroic mirrors each for transmitting or reflecting light in a short wavelength region including the wavelength region of the reflected laser beam.

6. A laser Raman microprobe according to claim 4, wherein said plurality of filters are band-pass filters each for transmitting or reflecting light in the wavelength region of the reflected laser beam.

7. A laser Raman microprobe according to claim 4, wherein said plurality of filters include at least one dichroic mirror for transmitting or reflecting light in a short wavelength region including the wavelength region of the reflected laser beam and a plurality of band-pass filters for transmitting or reflecting light in the wavelength region of the reflected laser beam.

8. A laser Raman microprobe according to claim 4, wherein said plurality of filters are radially arranged.

9. A laser Raman microprobe according to claim 4, wherein said plurality of filters are arranged in at least one line.

10. A laser Raman microprobe according to claim 4, comprising light detection means for detecting the reflected laser beam separated by said separation means, including an image pickup camera and drive means for driving said filters so as to successively locate one of said filters at an angle in said optical path and select a corresponding one of said filters in response to the maximum image output from said light detection means to thereby eliminate stray light due to the reflected laser beam in the Raman scattered light from the filter at maximum.

11. A laser Raman microprobe for analyzing a sample comprising:
    a microscope;
    a laser oscillator;
    laser directing means for directing a laser beam generated by said laser oscillator to the sample through said microscope;
    an optical system for passing along at least a portion thereof a laser beam reflected by the sample and applied to the microscope and Raman scattered light generated by the sample and applied to the microscope in combination,
    said optical system including at least a filter located at an angle in an optical path of the combined reflected laser beam and Raman scattered light passed from said microscope for reflecting light in a predetermined wavelength region and for transmitting light in another predetermined wavelength region so as to seperate the reflected laser beam and the Raman scattered light; and
    an analyzer including a single-monochromator coupled to said optical system for analyzing the sample based on a resulting spectrum;
    said filter enabling application of substantially only the separated Raman scattered light directly to said single-monochromator.

12. A laser Raman microprobe according to claim 11, wherein said filter is a dichroic mirror for reflecting the light in a short wavelength region including the wavelength region of the reflected laser beam.

13. A laser Raman microprobe according to claim 11, wherein said filter is a band-pass filter for reflecting the light in the wavelength region of the reflected laser beam.

14. A laser Raman microprobe according to claim 11, wherein said filter one of transmits and reflects light in a wavelength region of the reflected laser beam and one of reflects and transmits light in a wavelength region of the Raman scattered light, the Raman scattered light having a wavelength upon the wavelength of said laser osicillator.

* * * * *